United States Patent
Watanabe et al.

(10) Patent No.: US 7,041,846 B2
(45) Date of Patent: May 9, 2006

(54) ALICYCLIC METHACRYLATE HAVING OXYGEN SUBSTITUENT GROUP ON α-METHYL

(75) Inventors: Takeru Watanabe, Niigata-ken (JP); Jun Hatakeyama, Niigata-ken (JP); Takeshi Kinsho, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 110 days.

(21) Appl. No.: 10/791,843

(22) Filed: Mar. 4, 2004

(65) Prior Publication Data

US 2004/0176630 A1  Sep. 9, 2004

(30) Foreign Application Priority Data

Mar. 7, 2003  (JP) .............................. 2003-061476

(51) Int. Cl.
  *C07C 69/74* (2006.01)
  *C07C 69/75* (2006.01)
  *C07C 69/753* (2006.01)
(52) U.S. Cl. .................................... 560/128
(58) Field of Classification Search ................ 560/128
See application file for complete search history.

(56) References Cited

U.S. PATENT DOCUMENTS 6,080,524 A * 6/2000 Choi .................... 430/270.1
6,287,747 B1 * 9/2001 Choi et al. ............ 430/270.1

FOREIGN PATENT DOCUMENTS

| JP | 4-39665 A | 2/1992 |
|----|-----------|--------|
| JP | 2004-53822 A | 2/2004 |
| JP | 2004-118136 A | 4/2004 |
| JP | 2004-161860 A | 6/2004 |

* cited by examiner

*Primary Examiner*—Elvis O. Price
(74) *Attorney, Agent, or Firm*—Birch, Stewart, Kolasch & Birch, LLP

(57) ABSTRACT

Alicyclic methacrylate compounds having an oxygen substituent group on their α-methyl group, represented by formula (1), are novel wherein $R^1$ is H or $C_1$–$C_{10}$ alkyl which may contain a halogen atom, hydroxyl group, ether bond, carbonyl group, carboxyl group or cyano group, and $R^2$ is a monovalent $C_3$–$C_{20}$ organic group having an alicyclic structure. Polymers prepared from these alicyclic methacrylate compounds have improved transparency, especially at the exposure wavelength of an excimer laser, and improved dry etching resistance. Resist compositions comprising the polymers are sensitive to high-energy radiation, show a high resolution, allow smooth development, lend themselves to micropatterning, and are thus suitable as micropatterning material for VLSI fabrication

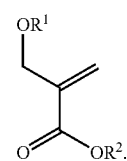

(1)

7 Claims, No Drawings

ALICYCLIC METHACRYLATE HAVING OXYGEN SUBSTITUENT GROUP ON α-METHYL

This Non-provisional application claims priority under 35 U.S.C. § 119(a) on Patent Application No(s). 2003-061476 filed in Japan on Mar. 7, 2003, the entire contents of which are hereby incorporated by reference.

This invention relates to novel alicyclic methacrylate compounds having an oxygen substituent group on their α-methyl group which are useful as monomers for polymerization to form base resins for use in micropatterning resist compositions.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

The resist materials for use in photolithography using light of an excimer laser, especially ArF excimer laser having a wavelength of 193 nm, are, of course, required to have a high transparency to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. There exists a strong demand to further improve resist materials.

Most common among high transparency resins used in the art are copolymers of acrylic or methacrylic acid derivatives. Active research works have been made on these copolymers to use them effectively as resist material. JP-A 4-39665 describes that an alicyclic structure such as adamantyl must be introduced as an ester substituent group into copolymers of acrylic or methacrylic acid derivatives in order to enhance the structural rigidity of the backbone and to provide necessary etching resistance. The introduction of an alicyclic structure, on the other hand, increases the water repellency of polymers, which disturbs smooth development with an aqueous tetramethylammonium hydroxide solution, a developer, tending to have deleterious effects of forming micropatterns with configuration defects and eventually incurring pattern disruption. When these polymers are formulated as the base resin into resist compositions, the resulting resist compositions in some cases have satisfactory resolution, but do not withstand etching, and in other cases, have acceptable etch resistance, but a low resolution and insufficient performance.

SUMMARY OF THE INVENTION

An object of the invention is to provide a novel alicyclic methacrylate compound having an oxygen substituent group on its α-methyl group which is useful as a monomer for polymerization to form a base resin for use in a micropatterning resist composition which is improved in both etching resistance and resolution when processed by photolithography using light with a wavelength of up to 300 nm, especially ArF excimer laser light as the light source.

It has been found that alicyclic methacrylate compounds having an oxygen substituent group on their α-methyl group, represented by the general formulae (1), (2) and (3) below, are readily synthesized in high yields, that polymers obtained through polymerization of these alicyclic methacrylate compounds having an oxygen substituent group on their α-methyl group have high transparency at the exposure wavelength of an excimer laser, and that resist compositions using the polymers as the base resin have improved etching resistance and resolution upon lithographic processing. Though not bound to the theory, it is believed that the alicyclic moiety in the inventive compounds largely contributes to the enhancement of etching resistance. With respect to the improvement in resolution, it is believed that the presence of an oxymethyl group in the inventive compounds increases the hydrophilicity in proximity to the polymer backbone, enabling more smooth development.

In a first aspect, the invention provides an alicyclic methacrylate having an oxygen substituent group on its α-methyl group, represented by the general formula (1).

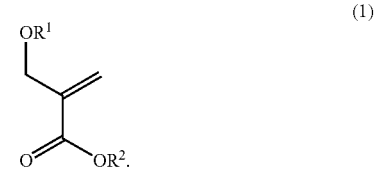

Herein $R^1$ is hydrogen or an alkyl group of 1 to 10 carbon atoms which may contain a halogen atom, hydroxyl group, ether bond, carbonyl group, carboxyl group or cyano group, and $R^2$ is a monovalent organic group of 3 to 20 carbon atoms having an alicyclic structure.

In a second aspect, the invention provides an alicyclic methacrylate having an oxygen substituent group on its α-methyl group, represented by the general formula (2).

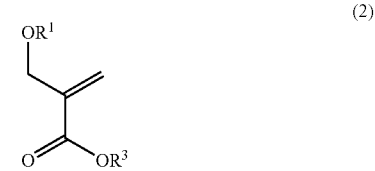

Herein $R^1$ is as defined above, and $R^3$ is a tertiary alkyl group of 4 to 20 carbon atoms having an alicyclic structure.

In a third aspect, the invention provides an alicyclic methacrylate having an oxygen substituent group on its α-methyl group, represented by the general formula (3).

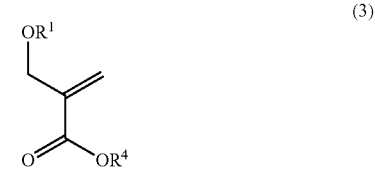

Herein R¹ is as defined above, and R⁴ is an organic group of 4 to 20 carbon atoms having a lactone structure.

DESCRIPTION OF THE PREFERRED EMBODIMENT

The alicyclic methacrylate compounds having an oxygen substituent group on their α-methyl group of the present invention have the general formulae (1), (2) and (3).

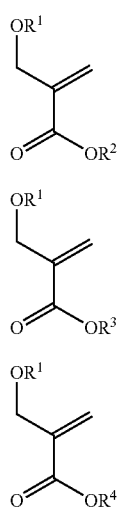

Herein, $R^1$ is hydrogen or an alkyl group of 1 to 10 carbon atoms which may contain a halogen atom, hydroxyl group, ether bond, carbonyl group, carboxyl group or cyano group. $R^2$ is a monovalent organic group of 3 to 20 carbon atoms having an alicyclic structure. $R^3$ is a tertiary alkyl group of 4 to 20 carbon atoms having an alicyclic structure. $R^4$ is an organic group of 4 to 20 carbon atoms having a lactone structure.

The $C_1$–$C_{10}$ alkyl group represented by $R^1$ may be either straight, branched or cyclic and contain a halogen atom, hydroxyl group, ether bond, carbonyl group, carboxyl group or cyano group. Suitable alkyl groups are illustrated by methyl, ethyl, propyl, 2-propyl, butyl, 2-butyl, isobutyl, t-butyl, pentyl, hexyl, cyclohexyl, decyl, chloromethyl, dichloromethyl, trichloromethyl, trifluoromethyl, 2-hydroxyethyl, 2-hydroxypropyl, methoxymethyl, ethoxymethyl, 2-methoxyethoxymethyl, 1-ethoxyethyl, 2-tetrahydropyranyl, formyl, acetyl, methoxyacetyl, acetoxyacetyl, cyanomethyl, and 2-cyanoethyl.

Examples of the $C_3$–$C_{20}$ monovalent organic group having an alicyclic structure represented by $R^2$ include cyclopropyl, cyclobutyl, cyclopentyl, cyclohexyl, cycloheptyl, dicycloheptyl, dicyclooctyl, dicyclononyl, dicyclodecanyl, tricyclodecanyl, adamantyl, tetracyclododecanyl, cyclohexylmethyl, dicycloheptylmethyl, isobornyl, menthyl, hydroxycyclohexyl, hydroxydicycloheptyl, and hydroxyadamantyl as well as those groups illustrated for $R^3$ and $R^4$ later.

Examples of the $C_4$–$C_{20}$ tertiary alkyl group having an alicyclic structure represented by $R^3$ include 1-methylcyclopropyl, 1-methylcyclopentyl, 1-ethylcyclopentyl, 1-methylcyclohexyl, 1-ethylcyclohexyl, 1-cyclopentylcyclopentyl, 1-cyclohexylcyclopentyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0²,⁶]decyl, 8-ethyl-8-tricyclo[5.2.1.0²,⁶]decyl, 3-methyl-3-tetracyclo[4.4.0.1²,⁵,1⁷,¹⁰]dodecyl, 3-ethyl-3-tetracyclo[4.4.0.1²,⁵,1⁷,¹⁰]dodecyl, 2-methyl-2-adamantyl, 2-ethyl-2-adamantyl, 1-adamantyl-1-methylethyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

Examples of the $C_4$–$C_{20}$ organic group having a lactone structure represented by $R^4$ include butyrolactonyl, valerolactonyl, 1,3-cyclohexanecarbolactonyl, 4-oxa-5-oxotricyclo[5.2.1.0²,⁶]decyl, 2,6-norbornanecarbolacton-3-ylmethyl, 2,6-norbornanecarbolacton-5-yl, 3-methoxycarbonyl-2,6-norbornanecarbolacton-5-yl, and 7-oxa-2,6-norbornanecarbolacton-5-yl.

By properly choosing $R^1$ and $R^2$, $R^3$ or $R^4$ in accordance with a particular application, it is possible to optimize the polarity and other properties of an overall molecule and eventually, the characteristics of a photoresist utilizing the inventive compound.

Illustrative, non-limiting, examples of the ester compounds of the invention are given below. In the following formulae, Me is methyl, Ac is acetyl and Et is ethyl.

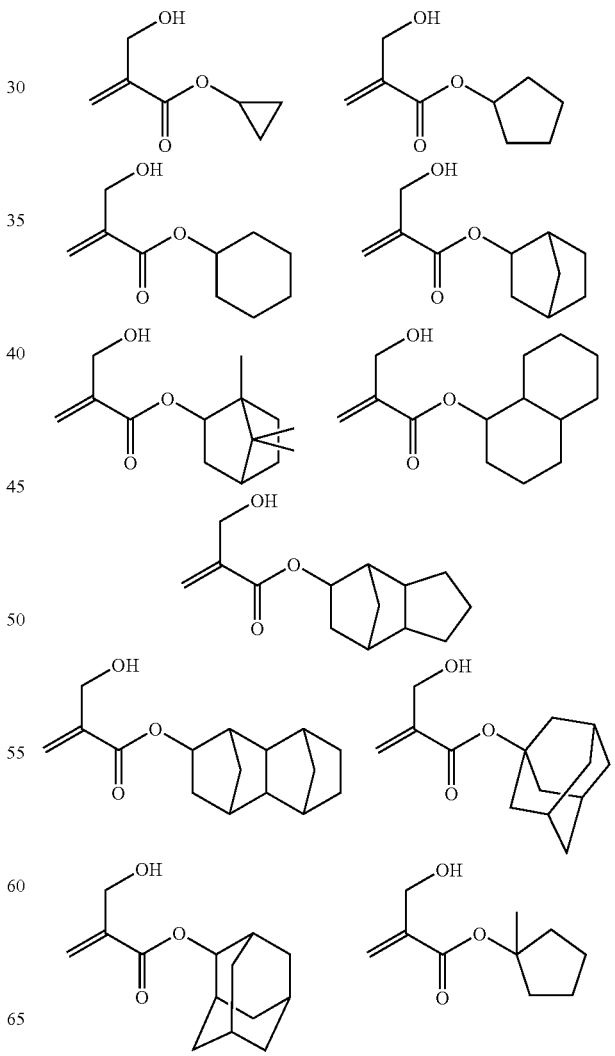

-continued
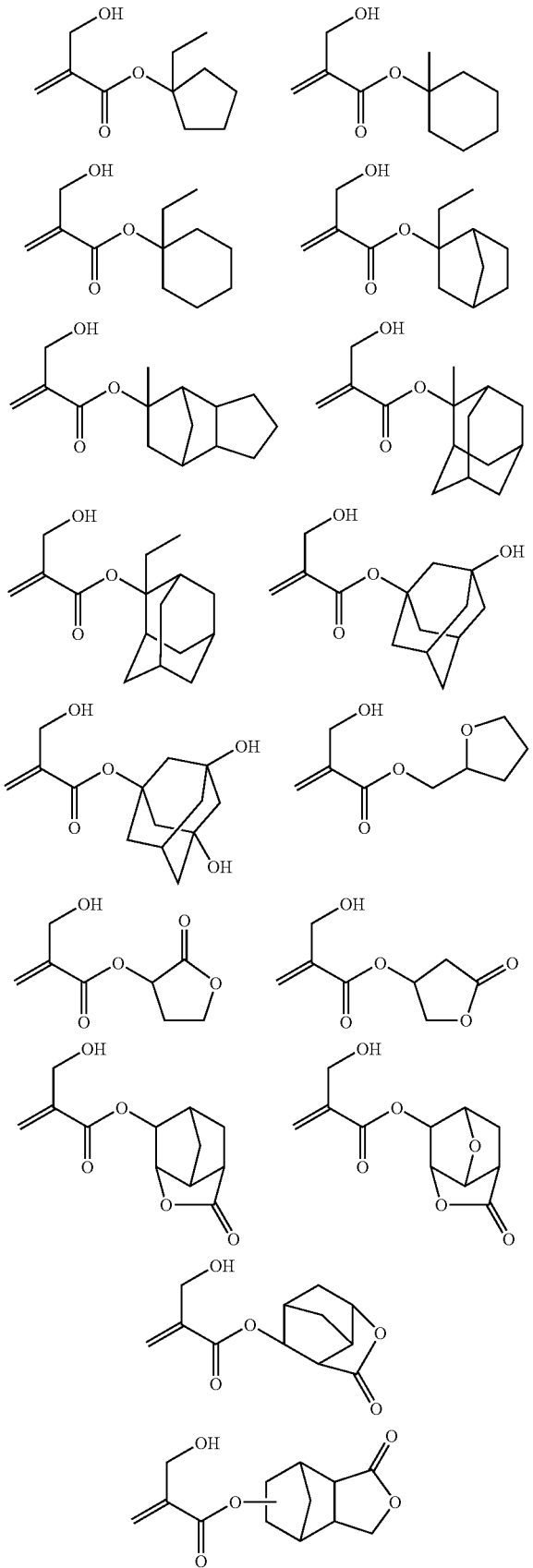
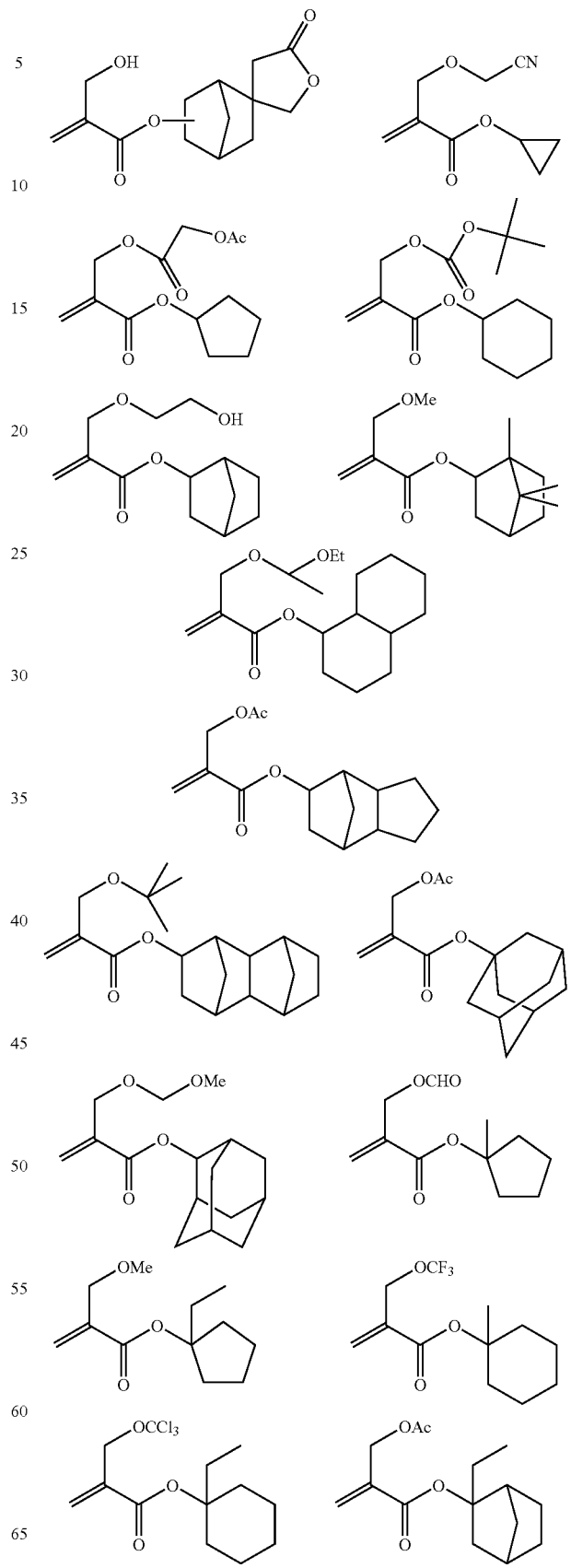

-continued

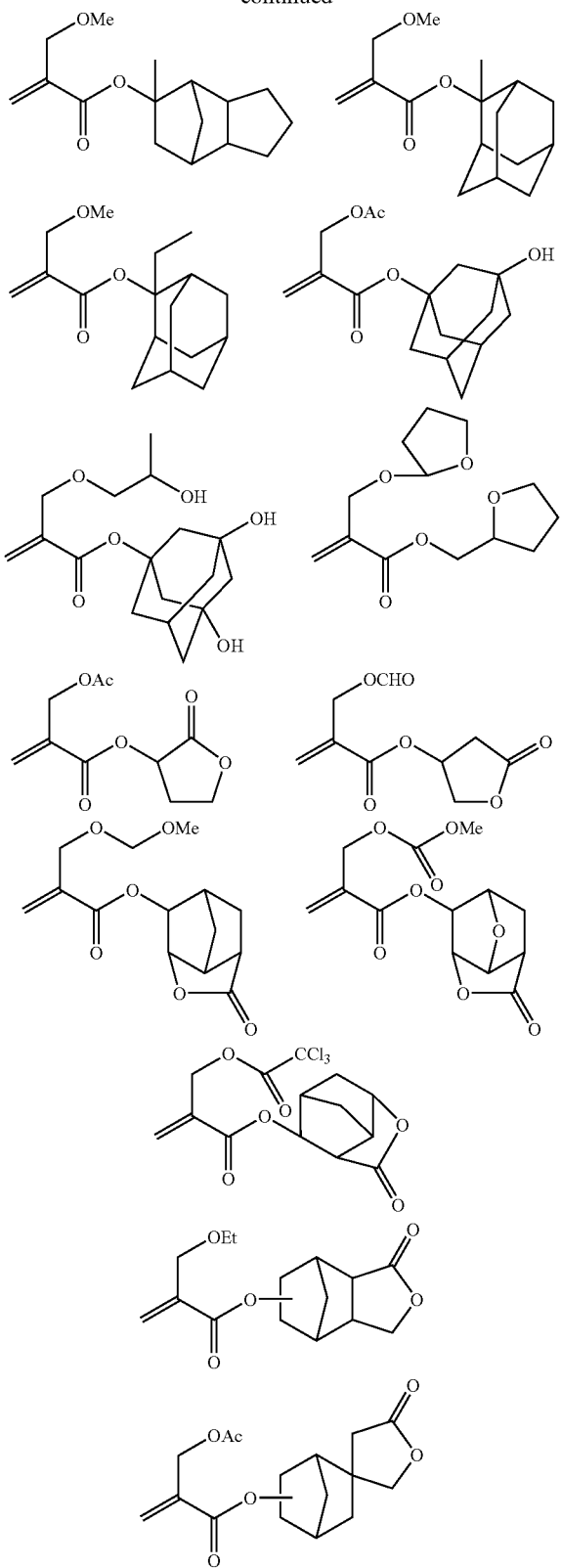

The alicyclic methacrylate compound having an oxygen substituent group on the α-methyl group, represented by the formula (1), according to the present invention can be prepared, for example, by the synthesis process described below. In the practice of the invention, the synthesis process is not limited thereto.

Reference is first made to the compound of formula (1) wherein $R^1$=H. It can be synthesized, as shown by the reaction scheme below, in one step from a corresponding acrylate compound of formula (4) which has been prepared by a routine process. This reaction is a hydroxymethylation of the acrylate compound at the α-position as shown below. One molar equivalent of a formaldehyde equivalent reacts on the acrylate compound of formula (4) in a solvent or solventless system in the presence of an amine compound to form an α-(hydroxymethyl)acrylate compound of formula (5).

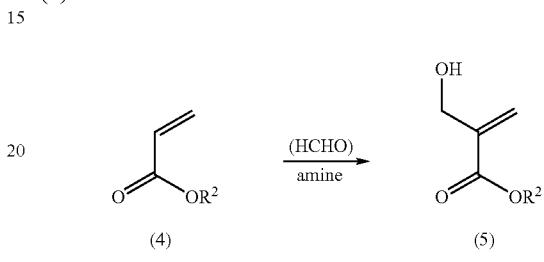

Herein $R^2$ is a monovalent $C_3$–$C_{20}$ organic group having an alicyclic structure.

The amine compound used in the hydroxymethylation is illustrated by trimethylamine, triethylamine, tributylamine, pyridine, 4-dimethylaminopyridine, 1,4-diazabicyclo[2.2.2] octane, 1,5-diazabicyclo[4.3.0]non-5-ene, and 1,8-diazabicyclo[5.4.0]undec-7-ene. An appropriate amount of the amine compound used is 0.001 to 10 moles, especially 0.01 to 1 mole per mole of the starting reactant. With less than 0.001 mole of the amine, the reaction may not proceed. More than 10 moles of the amine is wasteful because no further effect corresponding to such an excess may be exerted.

The formaldehyde equivalent is illustrated by gaseous formaldehyde, formalin, paraformaldehyde and 1,3,5-trioxane. An appropriate amount of the formaldehyde equivalent used is 0.2 to 10 moles, especially 0.5 to 2 moles of formaldehyde per mole of the starting reactant. With less than 0.2 mole of formaldehyde, a large portion of the starting reactant, acrylate compound may be left, leading to very low yields. More than 10 moles of formaldehyde can form a large amount of by-product, also leading to very low yields.

Examples of the solvent, if used in the hydroxymethylation, include hydrocarbons such as toluene, hexane and heptane; ethers such as dibutyl ether, diethylene glycol diethyl ether and tetrahydrofuran; alcohols such as methanol and ethanol; halogenated hydrocarbons such as methylene chloride; esters such as ethyl acetate; ketones such as acetone and 2-butanone; nitriles such as acetonitrile; and aprotic polar solvents such as dimethyl sulfoxide, N,N-dimethylformamide and N,N-dimethylacetamide; and water. These solvents may be used alone or in admixture of any.

The temperature for the hydroxymethylation is preferably in the range of about −20° C. to about 100° C. An appropriate reaction temperature may be selected in the range depending on the reactants and reaction conditions. In an instance where reaction is effected in water using 1,4-diazabicyclo[2.2.2]octane as the amine compound and formaldehyde as the formaldehyde equivalent, a temperature in the range of 0° C. to 60° C. is preferred. As the reaction temperature raises, more side reactions occur and more formaldehyde is evaporated off. It is thus important for achieving high yields to perform the reaction at a permissible lower temperature within the range where the reaction proceeds at a practically acceptable rate.

For increased yields, the reaction time is desirably determined by monitoring the progress of reaction by thin-layer chromatography (TLC), gas chromatography (GC) or the like. The reaction time is usually about 1 to about 200 hours.

At the end of reaction, the target compound (5), α-(hydroxymethyl)acrylate compound is recovered by a conventional aqueous workup. The target compound (5) can be purified by any conventional technique such as recrystallization, chromatography or distillation.

Next reference is made to the compound of formula (1) wherein $R^1$ is a $C_1$–$C_{10}$ alkyl group which may contain a halogen atom, hydroxyl group, ether bond, carbonyl group, carboxyl group or cyano group. By subjecting the above-obtained α-(hydroxymethyl)acrylate compound of formula (5) to alkylation or acylation in a conventional way, as shown by the reaction scheme below, an target compound of formula (6) can be synthesized. The resulting α-(alkoxymethyl) or α-(acyloxymethyl)acrylate compound of formula (6) can be purified by any conventional technique such as recrystallization, chromatography or distillation.

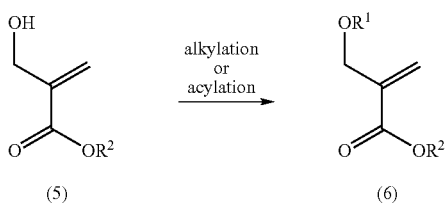

Herein, $R^1$ is a $C_1$–$C_{10}$ alkyl group which may contain a halogen atom, hydroxyl group, ether bond, carbonyl group, carboxyl group or cyano group; and $R^2$ is a monovalent $C_3$–$C_{20}$ organic group having an alicyclic structure.

The inventive alicyclic methacrylate compounds having an oxygen substituent group on their α-methyl group are useful as monomers to form polymers which serve effectively as the base resin in photoresist compositions.

Preparation of a polymer using the inventive alicyclic methacrylate compound as a monomer is generally carried out by mixing the monomer with a solvent, adding a catalyst or polymerization initiator thereto, and effecting polymerization reaction while heating or cooling if necessary. This polymerization may be done by any conventional technique such as radical, cationic and anionic polymerization techniques. One or more other compounds having a polymerizable double bond can be copolymerized if necessary.

The polymer resulting from the above-described polymerization is used as a base resin to formulate a resist composition. The resist composition is generally formulated by adding an organic solvent and a photoacid generator to the base resin. If necessary, a crosslinking agent, a basic compound, a dissolution inhibitor and the like are further added. Preparation of resist compositions may be done in a conventional way.

EXAMPLE

Examples of the invention are given below by way of illustration and not by way of limitation. In the formulae below, Me is methyl and Ac is acetyl.

Example 1

Synthesis of 2,6-norbornanecarbolacton-5-yl α-(hydroxy-methyl)acrylate

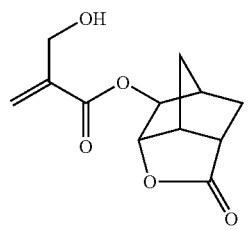

118 g of 2,6-norbornanecarbolacton-5-yl acrylate, 31.8 g of 1,4-diazabicyclo[2.2.2]octane, 50.6 g of 37% formalin and 250 g of tetrahydrofuran were combined and stirred for 20 hours. The reaction solution was neutralized with hydrochloric acid, followed by conventional aqueous workup. The solvent was distilled off in vacuo, after which the product was purified by silica gel chromatography, obtaining 81.0 g (yield 60%) of 2,6-norbornanecarbolacton-5-yl α-(hydroxymethyl)acrylate represented by formula (7).

Results of IR and NMR analyses

IR (thin film): ν=3479, 2980, 2883, 1782, 1716, 1637, 1452, 1396, 1342, 1308, 1267, 1180, 1163, 1151, 1057, 1043, 1028, 1012, 998, 954 cm$^{-1}$ $^1$H-NMR (600 MHz in CDCl$_3$): δ=1.58 (1H, br. d, J=11.6 Hz), 1.69 (1H, br. d, J=13.8 Hz), 1.93 (1H, br. d, J=11.6 Hz), 1.97 (1H, ddd, J=13.7, 11.3, 4.5 Hz), 2.24 (1H, br. s), 2.46–2.52 (2H, m), 3.14 (1H, m), 4.23 (2H, s), 4.49 (1H, d, J=4.8 Hz), 4.58 (1H, m), 5.81 (1H, d, J=1.0 Hz), 6.15 (1H, d, J=1.0 Hz)

Example 2

Synthesis of 2,6-norbornanecarbolacton-5-yl α-(methoxy-methoxymethyl)acrylate

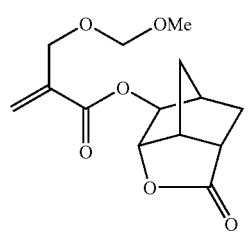

With stirring, 9.7 g of chloromethyl methyl ether was added to a mixture of 23.8 g of 2,6-norbornanecarbolacton-5-yl α-(hydroxymethyl)acrylate obtained in Example 1, 15.2 g of triethylamine and 200 g of acetonitrile. After 20 hours of stirring, water was added to the reaction solution to stop the reaction. This was followed by conventional aqueous workup. The solvent was distilled off in vacuo, after which the product was purified by silica gel chromatography, obtaining 22.0 g (yield 78%) of 2,6-norbornanecarbolacton-5-yl α-(methoxymethoxymethyl)acrylate represented by formula (8).

Example 3

Synthesis of 1-ethylcyclopentyl α-(hydroxymethyl)acrylate

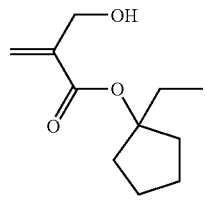

(9)

Reaction was performed as in Example 1 except that 95.4 g of 1-ethylcyclopentyl acrylate was used instead of 2,6-norbornanecarbolacton-5-yl acrylate. Purification by vacuum distillation (boiling point 82° C./30 Pa) gave 1-ethylcyclopentyl α-(hydroxymethyl)acrylate represented by formula (9). The yield was 68%.

Results of IR and NMR analyses

IR (thin film): ν=3466, 2970, 2877, 1707, 1635, 1462, 1392, 1336, 1273, 1227, 1163, 1113, 1055, 949 cm$^{-1}$ $^1$H-NMR (600 MHz in CDCl$_3$): δ=0.86 (3H, m), 1.56–1.76 (6H, m), 2.01 (2H, m), 2.14 (2H, m), 2.61 (1H, br), 4.28 (2H, s), 5.74 (1H, m), 6.16 (1H, m)

Example 4

Synthesis of 1-ethylcyclopentyl α-(methoxymethyl)acrylate

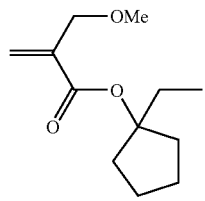

(10)

A mixture of 19.8 g of 1-ethylcyclopentyl α-(hydroxymethyl)acrylate, 40.0 g of methyl iodide, 30.0 g of silver (I) oxide and 50 g of N,N-dimethylformamide was stirred at 50° C. for 30 hours. The solids were filtered off, followed by conventional aqueous workup. The solvent was distilled off in vacuo. Purification by distillation (boiling point 53° C./16 Pa) gave 1-ethylcyclopentyl α-(methoxymethyl)acrylate represented by formula (10). The yield was 62%.

Results of IR and NMR analyses

IR (thin film): ν=2970, 1939, 2877, 2835, 2816, 1720, 1709, 1637, 1460, 1396, 1323, 1277, 1161, 1113, 948 cm$^{-1}$ $^1$H-NMR (600 MHz in CDCl$_3$): δ=0.86 (3H, t, J=7.6 Hz), 1.58–1.75 (6H, m), 2.00 (2H, q, J=7.6 Hz), 2.14 (2H, m), 3.38 (3H, s), 4.09 (2H, dd), 5.76 (1H, dt), 6.20 (1H, dt)

Example 5

Synthesis of 8-tricyclo[5.2.1.0$^{2,6}$]decyl α-(hydroxymethyl)-acrylate

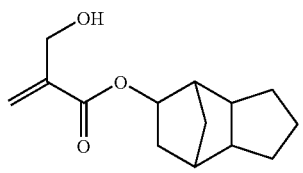

(11)

The procedure of Example 1 was repeated except that 117 g of 8-tricyclo[5.2.1.0$^{2,6}$]decyl acrylate was used instead of 2,6-norbornanecarbolacton-5-yl acrylate. There was obtained 8-tricyclo[5.2.1.0$^{2,6}$]decyl α-(hydroxymethyl)acrylate represented by formula (11). The yield was 60%.

Results of IR and NMR analyses

IR (thin film): ν=3467, 2949, 2862, 1709, 1635, 1475, 1448, 1396, 1309, 1267, 1223, 1157, 1134, 1055, 1022, 984, 947 cm$^{-1}$ $^1$H-NMR (600 MHz in CDCl$_3$): δ=0.88–1.00 (2H, m), 1.22 (1H, dtt, J=12.4, 12.4, 6.9 Hz), 1.29 (1H, m), 1.36 (1H, m), 1.45 (1H, ddd, J=13.4, 4.5, 2.1 Hz), 1.63–1.72 (2H, m), 1.73–1.90 (4H, m), 2.04 (1H, d, J=4.5 Hz), 2.11 (1H, s), 2.40 (1H, br. s), 4.30 (2H, s), 4.65 (1H, J=7.2 Hz), 5.78 (1H, m), 6.19 (1H, d, J=1.0 Hz)

Example 6

Synthesis of 8-tricyclo[5.2.1.0$^{2,6}$]decyl α-(acetoxymethyl)-acrylate

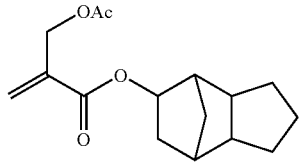

(12)

To a mixture of 23.6 g of 8-tricyclo[5.2.1.0$^{2,6}$]decyl α-(hydroxymethyl)acrylate and 15.8 g of pyridine was added 15.3 g of acetic anhydride. The mixture was stirred for 20 hours. Water was added to the reaction solution to stop the reaction, followed by conventional aqueous workup. The solvent was distilled off in vacuo. Purification by distillation (boiling point 123° C./13 Pa) gave 23.7 g (yield 90%) of 8-tricyclo[5.2.1.0$^{2,6}$]decyl α-(acetoxymethyl)acrylate represented by formula (12).

Results of IR and NMR analyses

IR (thin film): ν=2951, 2864, 1749, 1722, 1643, 1475, 1448, 1400, 1369, 1311, 1271, 1228, 1184, 1167, 1157, 1134, 1047, 982, 953 cm$^{-1}$ $^1$H-NMR (600 MHz in CDCl$_3$): δ=0.88–0.99 (2H, m), 1.21 (1H, dtt, J=12.4, 12.4, 6.5 Hz), 1.28 (1H, dt, J=10.3, 1.2 Hz), 1.35 (1H, br. d, J=10.3 Hz), 1.44 (1H, ddd, J=13.4, 4.5, 2.1 Hz), 1.62–1.70 (2H, m), 1.72–1.89 (4H, m), 2.03 (1H, d, J=4.5 Hz), 2.08 (3H, s), 2.11 (1H, br. s), 4.65 (1H, br. d, J=6.9 Hz), 4.77 (2H, br. s), 5.78 (1H, m), 6.31 (1H, d, J=1.0 Hz)

Example 7

Synthesis of 1-adamantyl α-(hydroxymethyl)acrylate

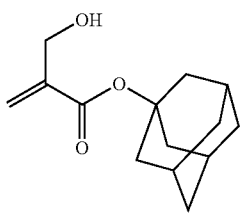

The procedure of Example 1 was repeated except that 117 g of 1-adamantyl acrylate was used instead of 2,6-norbornanecarbolacton-5-yl acrylate. There was obtained 1-adamantyl α-(hydroxymethyl)acrylate represented by formula (13) (yield 60%).

Reference Example 1

Synthesis of a Polymer using Inventive α-(oxymethyl)acrylic Acid Ester

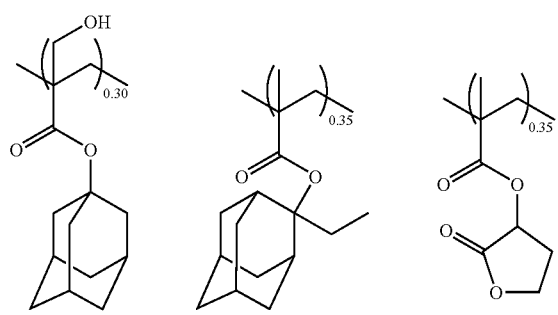

In a nitrogen atmosphere, a mixture of 7.1 g of 1-adamantyl α-(hydroxymethyl)acrylate obtained in Example 7, 8.7 g of 2-ethyl-2-adamantyl methacrylate, 6.0 g of 2-oxotetrahydrofuran-3-yl methacrylate, 60 mg of N,N'-azobisisobutyronitrile, and 80 ml of tetrahydrofuran was heated and stirred at 60° C. for 20 hours. After cooling, the reaction mixture was added dropwise to 2 liters of methanol under vigorous stirring. The precipitate which settled down was collected by filtration. The solids were washed with methanol and dried in vacuo, obtaining 16.4 g of the target polymer of formula (14). The yield was 75%. An component ratio calculated from its $^1$H-NMR spectrum indicated a copolymerization ratio of approximately 30:35:35. GPC analysis using polystyrene standards indicated a weight average molecular weight (Mw) of 9,800 and a polydispersity index (Mw/Mn) of 1.80.

Reference Example 2

Resist Pattern Formation using Polymer

Using the polymer obtained in Reference Example 1, a resist material was prepared. Its composition was:
(A) 80 parts by weight of the polymer of Reference Example 1 as a base polymer,
(B) 1.0 part by weight of triphenylsulfonium trifluoromethanesulfonate as a photoacid generator,
(C) 480 parts by weight of propylene glycol monomethyl ether acetate as a solvent, and
(D) 0.08 part by weight of tributylamine as a basic compound.

This was passed through a Teflon® filter having a pore diameter of 0.2 μm. The resist solution was spin coated on a silicon wafer having hexamethyldisilazane sprayed thereon at 90° C. for 40 seconds and heat treated at 120° C. for 90 seconds, forming a resist film of 500 nm thick. The resist film was exposed to ArF excimer laser light, heat treated at 120° C. for 90 seconds, cooled down to 23° C., and dipped in a 2.38% tetramethylammonium hydroxide aqueous solution at 23° C. for 60 seconds for development, thereby forming a 1:1 line-and-space pattern. The wafer as developed was observed under top-down SEM. Patterns down to a line width of 0.13 μm existed without collapse or stripping and hence, resolved. This demonstrates that the photoresist material of the invention has improved resolution.

Reference Example 3

Transparency of Polymer

The polymer obtained in Reference Example 1, 1.0 g, was dissolved in 6.0 g of cyclohexanone, which was passed through a Teflon® filter having a pore diameter of 0.2 μm. The solution was spin coated on a quartz substrate and heat treated at 90° C. for 60 seconds, forming a thin film of 500 nm thick. The thin film was measured for transmittance at 193 nm using a UV-visible spectrophotometer, finding a transmittance of 76% per 500 nm of film thickness. This result demonstrates that the polymer according to the invention has a sufficient transparency as the photoresist base polymer for excimer laser photolithography.

Reference Example 4

Etching Resistance of Polymer

The polymer obtained in Reference Example 1, 2 g, was dissolved in 10 g of cyclohexanone, which was passed through a Teflon® filter having a pore diameter of 0.2 μm. The solution was spin coated on a silicon wafer and heat treated at 90° C. for 60 seconds, forming a thin film of 700 nm thick. Using a reactive ion etching apparatus, the thin film was etched with $CF_4$ gas under conditions: power 100 W, pressure 5 Pa, and gas flow rate 30 ml/min. As a result, the etching rate was 1.10 based on a rate of 1.00 normalized for novolac resist. For comparison purposes, the same test was done on poly(p-hydroxystyrene) used as the base polymer for KrF resist, finding an etching rate of 1.20. These results demonstrate that the polymer according to the invention has a slower etching rate with $CF_4$ gas, that is, better dry etching resistance.

There have been described alicyclic methacrylate compounds having an oxygen substituent group on their α-methyl group which are very advantageous as monomers to form polymers having improved transparency, especially at the exposure wavelength of an excimer laser, and improved dry etching resistance. Resist compositions comprising polymers of the inventive monomers are sensitive to high-energy radiation, show a high resolution, allow smooth development and thus lend themselves to micropatterning. The resist compositions are thus suitable as micropatterning material for VLSI fabrication. Accordingly, the inventive alicyclic methacrylate compounds having an oxygen substituent group on their α-methyl group are quite useful as monomers to form base polymers for resist compositions in satisfying both the resolution and etching resistance of resist.

Japanese Patent Application No. 2003-061476 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An alicyclic methacrylate having an oxygen substituent group on its x-methyl group, represented by the general formula (1):

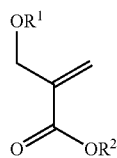
(1)

wherein $R^1$ is hydrogen, an alkyl group of 1 to 10 carbon atoms that is optionally interrupted by one or more from the group consisting of halogen atom, oxygen, alkoxy, carbonyl group, carboxyl group and cyano group, or an alkyl group of 1 to 10 carbon atoms optionally substituted by one or more from the group consisting of halogen atom, hydroxyl group, alkoxy, carbonyl group, carboxyl group and cyano group, and $R^2$ is a monovalent organic group of 3 to 20 carbon atoms having an alicyclic structure.

2. An alicyclic methacrylate having an oxygen substituent group on its α-methyl group, represented by the general formula (2):

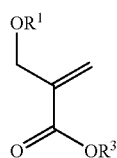
(2)

wherein $R^1$ is hydrogen or an alkyl group of 1 to 10 carbon atoms that is optionally interrupted by one or more from the group consisting of halogen atom, oxygen, alkoxy, carbonyl group, carboxyl group and cyano group, or an alkyl group of 1 to 10 carbon atoms optionally substituted by one or more from the group consisting of halogen atom, hydroxyl group, alkoxy, carbonyl group, carboxyl group and cyano group, and $R^3$ is a tertiary alkyl group of 4 to 20 carbon atoms having an alicyclic structure.

3. An alicyclic methacrylate having an oxygen substituent group on its α-methyl group, represented by the general formula (3):

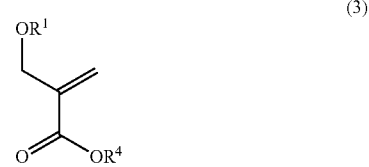

wherein $R^1$ is hydrogen or an alkyl group of 1 to 10 carbon atoms that is optionally interrupted by one or more from the group consisting of halogen atom, oxygen, alkoxy, carbonyl group, carboxyl group and cyano group, or an alkyl group of 1 to 10 carbon atoms optionally substituted by one or more from the group consisting of halogen atom, hydroxyl group, alkoxy, carbonyl group, carboxyl group and cyano group, and $R^4$ is an organic group of 4 to 20 carbon atoms having a lactone structure.

4. An alicyclic methacrylate having on its α-methyl group an oxygen substituent group selected from the group consisting of

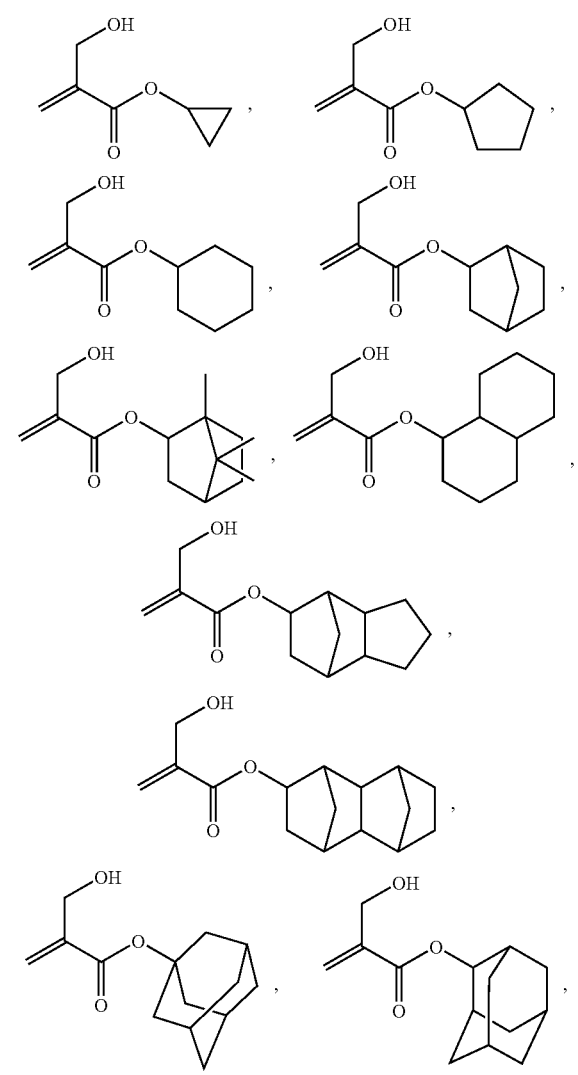

-continued
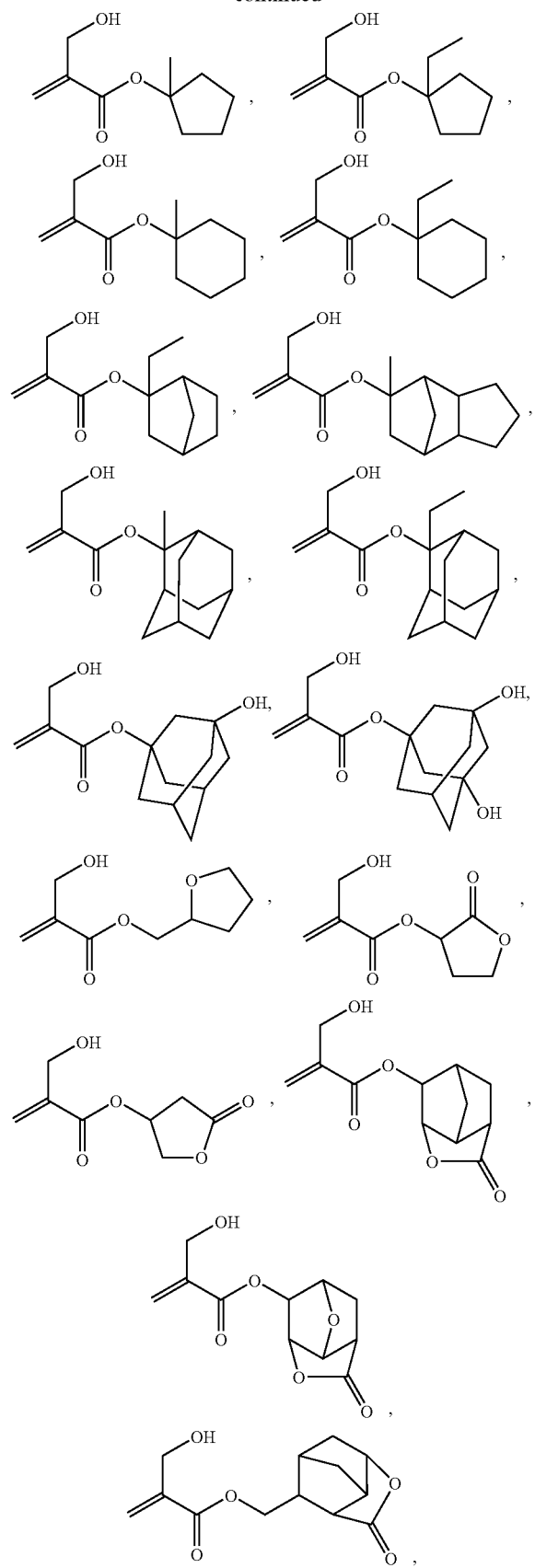
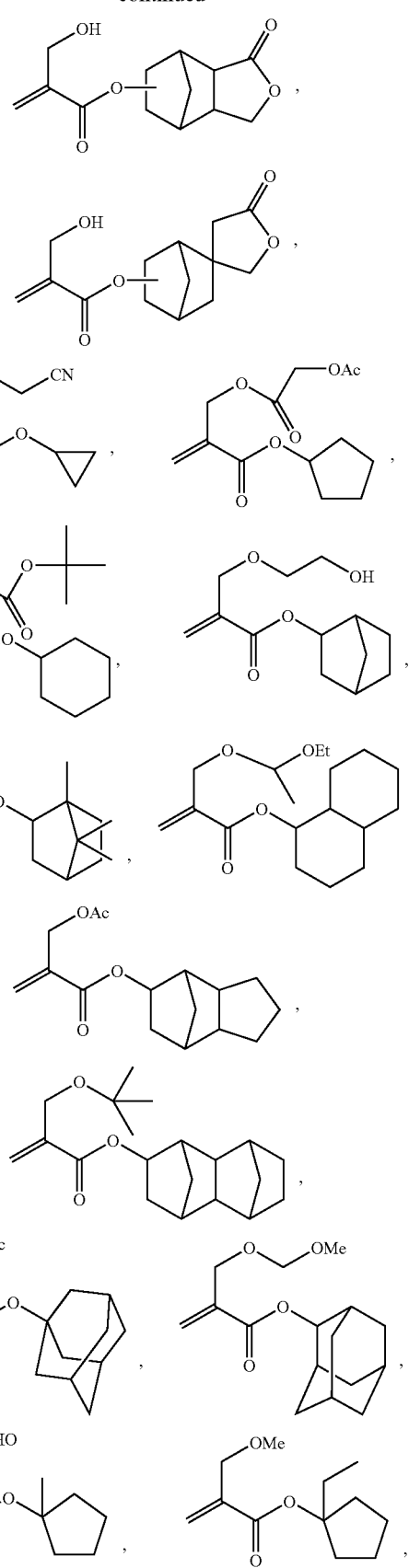

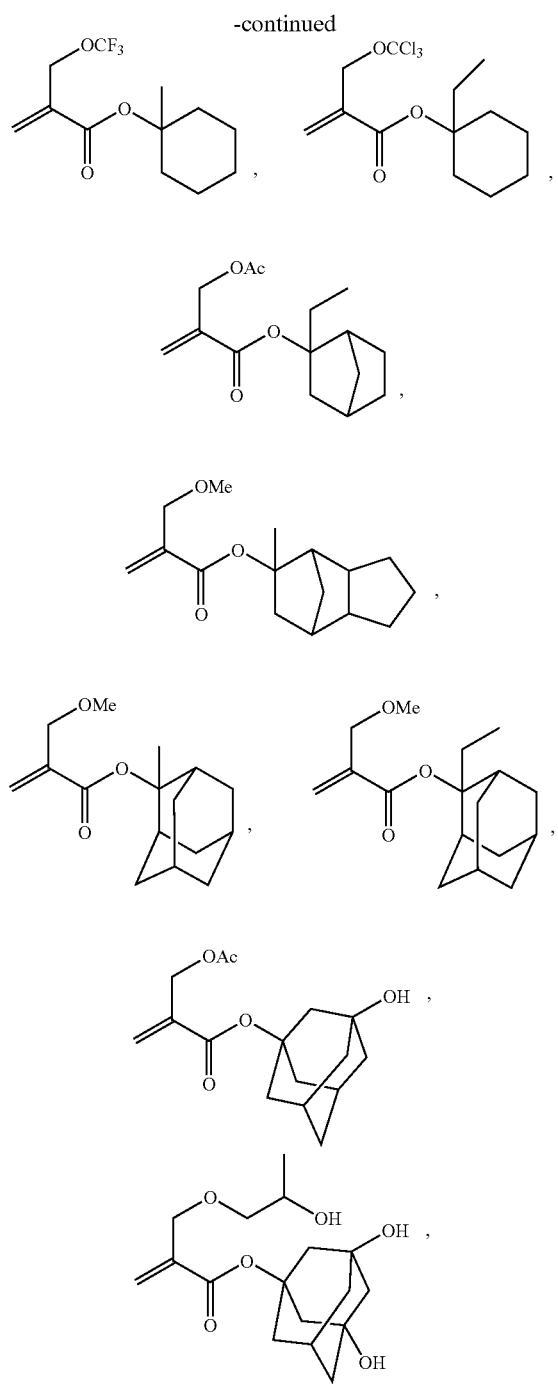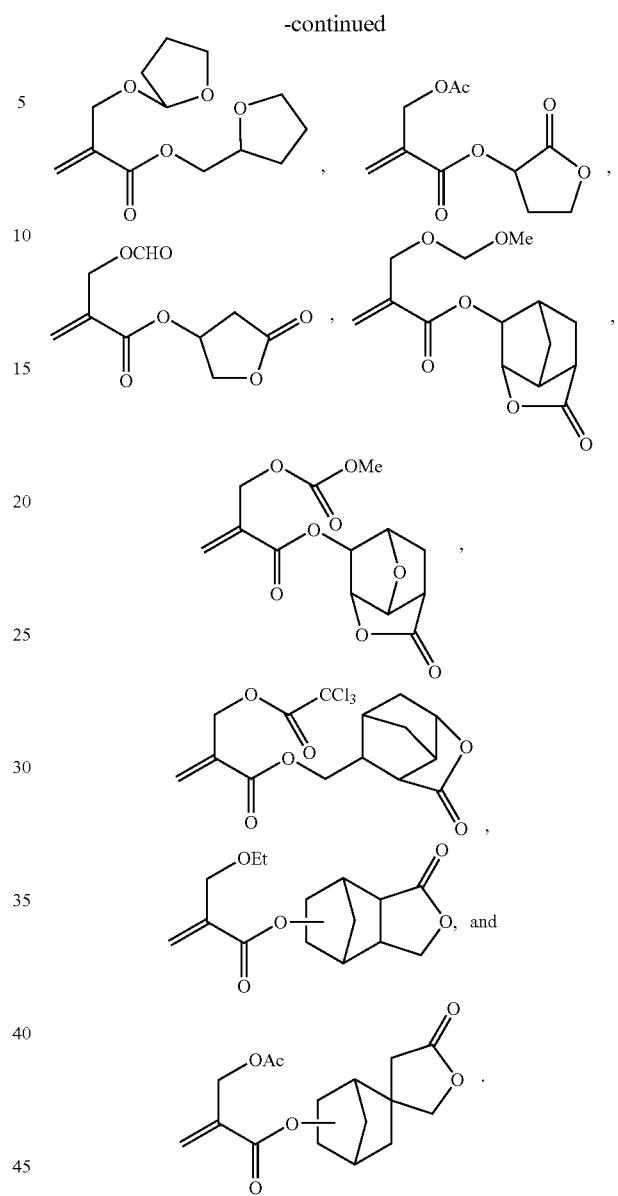
5. The alicyclic methacrylate of claim 1 wherein in Formula (1) the alkoxy is from 1–2 carbon atoms.
6. The alicyclic methacrylate of claim 2 wherein in Formula (2) the alkoxy is from 1–2 carbon atoms.
7. The alicyclic methacrylate of claim 3 wherein in Formula (3) the alkoxy is from 1–2 carbon atoms.
* * * * *